(12) United States Patent
Watanabe et al.

(10) Patent No.: US 10,249,412 B2
(45) Date of Patent: Apr. 2, 2019

(54) COMPOSITE CABLE

(71) Applicant: Hitachi Metals, Ltd., Tokyo (JP)

(72) Inventors: Takanobu Watanabe, Tokyo (JP); Detian Huang, Tokyo (JP); Haruyuki Watanabe, Tokyo (JP); Kimika Kudo, Tokyo (JP)

(73) Assignee: HITACHI METALS, LTD., Tokyo (JP)

( * ) Notice: Subject to any disclaimer, the term of this patent is extended or adjusted under 35 U.S.C. 154(b) by 0 days.

(21) Appl. No.: 15/730,383

(22) Filed: Oct. 11, 2017

(65) Prior Publication Data

US 2018/0151272 A1 May 31, 2018

(30) Foreign Application Priority Data

Nov. 25, 2016 (JP) .................... 2016-229204

(51) Int. Cl.
| | |
|---|---|
| H01B 11/04 | (2006.01) |
| H01B 11/02 | (2006.01) |
| G02B 6/44 | (2006.01) |
| H01B 1/04 | (2006.01) |
| H01B 7/04 | (2006.01) |
| H01B 9/00 | (2006.01) |
| H01B 11/20 | (2006.01) |
| H01B 13/02 | (2006.01) |
| B29L 31/34 | (2006.01) |

(52) U.S. Cl.
CPC ......... H01B 11/02 (2013.01); G02B 6/4401 (2013.01); H01B 1/04 (2013.01); H01B 7/048 (2013.01); H01B 9/005 (2013.01); H01B 11/20 (2013.01); H01B 13/02 (2013.01); *B29L 2031/3462* (2013.01)

(58) Field of Classification Search
CPC ................. H01B 11/04; H01B 11/06
USPC .......................... 174/113 R, 106 R
See application file for complete search history.

(56) References Cited

U.S. PATENT DOCUMENTS

| | | | | |
|---|---|---|---|---|
| 2,604,509 A | * | 7/1952 | Blanchard | H01B 7/046 138/130 |
| 3,651,243 A | * | 3/1972 | Hornor | H01B 11/20 174/103 |
| 6,792,316 B2 | * | 9/2004 | Sass | A61N 1/05 600/373 |
| 2012/0097419 A1 | * | 4/2012 | Varkey | H01B 7/046 174/106 R |
| 2012/0222869 A1 | * | 9/2012 | Varkey | E21B 23/14 166/385 |
| 2012/0292079 A1 | | 11/2012 | Muramatsu et al. | |
| 2013/0167502 A1 | * | 7/2013 | Wilson | B29C 70/025 57/210 |

FOREIGN PATENT DOCUMENTS

JP         2013-176567 A      9/2013

* cited by examiner

*Primary Examiner* — Chau N Nguyen
(74) *Attorney, Agent, or Firm* — McGinn I.P. Law Group, PLLC.

(57) ABSTRACT

A composite cable includes a twisted wire formed by twisting a plurality of signal lines, and a plurality of power lines that are arranged on a circumference of a circle concentric with the twisted wire so as to surround an outer circumference of the twisted wire and are twisted around the twisted wire.

10 Claims, 2 Drawing Sheets

COMPOSITE CABLE

The present application is based on Japanese patent application No. 2016-229204 filed on Nov. 25, 2016, the entire contents of which are incorporated herein by reference.

BACKGROUND OF THE INVENTION

1. Field of the Invention

The invention relates to a composite cable.

2. Description of the Related Art

A composite cable provided with signal lines and power lines has been proposed. In the composite cable, the signal lines and the power lines are twisted together in a mixed state (see e.g. JP 2013/176567). The composite cable is sometimes used as a cable for connecting, e.g. a camera head to a control unit in an endoscopic device.

SUMMARY OF THE INVENTION

The composite cable used for the endoscopic device is required to have a small diameter. Also, the composite cable used for the endoscopic device is required to be unbroken (i.e., to have a good flex resistance) even under repeated bending with a small bend radius r.

It is an object of the invention to provide a composite cable that has a good flex resistance as well as a small diameter.

According to an embodiment of the invention, a composite cable comprises:

a twisted wire formed by twisting a plurality of signal lines; and a plurality of power lines that are arranged on a circumference of a circle concentric with the twisted wire so as to surround an outer circumference of the twisted wire and are twisted around the twisted wire.

Effects of the Invention

According to an embodiment of the invention, a composite cable can be provided that has a good flex resistance as well as a small diameter.

BRIEF DESCRIPTION OF THE DRAWINGS

Next, the present invention will be explained in more detail in conjunction with appended drawings, wherein.

DETAILED DESCRIPTION OF THE PREFERRED EMBODIMENTS

Embodiment of the Invention (1) Configuration of Composite Cable

The configuration of a composite cable in an embodiment of the invention will be described below in reference to the drawings.

Figure 1A:
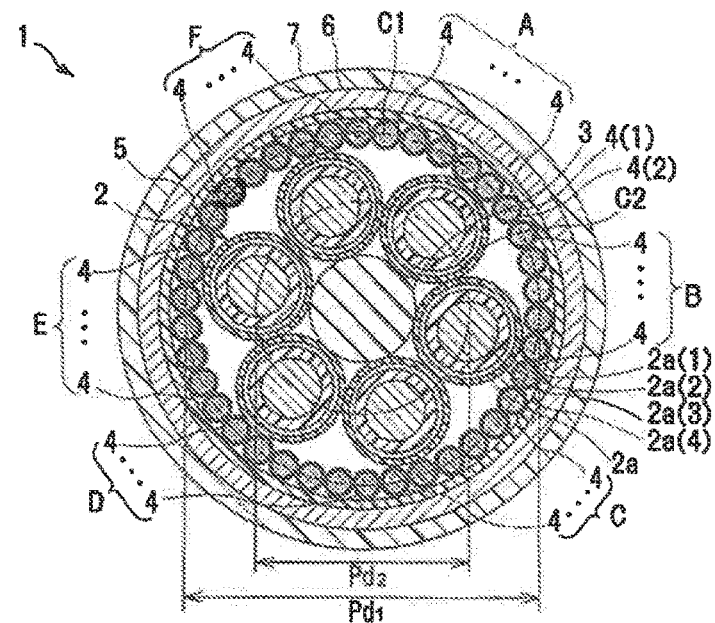
FIG. 1A is a schematic radial cross-sectional view showing an example of a composite cable in an embodiment of the present invention.

As shown in FIG. 1A, a composite cable 1 in the present embodiment has a twisted wire 2 (hereinafter, also referred to as "twisted signal wire 2") formed by twisting plural (e.g., six in the present embodiment) signal lines $2a$ together. For example, as the signal line $2a$, it is possible to use a coaxial line (coaxial cable) having a conductor $2a(1)$, an insulation layer $2a(2)$ provided around the conductor $2a(1)$, and a shield $2a(3)$ provided around the insulation layer $2a(2)$. As the conductor $2a(1)$, it is possible to use, e.g., a copper wire (solid wire, strand) or a stranded conductor formed by twisting plural copper wires. The insulation layer $2a(2)$ is preferably formed of a material with a low dielectric constant and a low dielectric loss tangent to reduce signal transmission loss. Such material which can be used here is, e.g., a fluorine-containing resin such as perfluoroalkoxy alkane (PFA) or polytetrafluoroethylene (PTFE), and a resin material such as polyethylene (PE). As the shield $2a(3)$, it is possible to use, e.g., a copper wire (solid wire, strand) or a stranded conductor formed by twisting plural copper wires. Alternatively, a braided shield formed by braiding the above-mentioned copper wires can be also used as the shield $2a(3)$. A non-conductor (jacket) $2a(4)$ may be additionally provided around the shield $2a(3)$.

An insert 3 (filler, insulating thread or insulating spacer, etc., and for example, hemp string) having insulating properties, if required, is preferably provided at the center of the twisted signal wire 2 so that the composite cable 1 can have a perfectly circular cross-section. In other words, the signal lines $2a$ are preferably arranged so as to surround the insert 3 (so that the insert 3 is located at the center). The insert 3 may be regarded as a part of the twisted signal wire 2.

Plural (e.g., thirty eight in the present embodiment) power lines 4 are arranged around the twisted signal wire 2 and are twisted about the twisted signal wire 2. The plural power lines 4 are annularly arranged so as to be located on a circumference of a circle C1 concentric with a circle C2 passing through the centers of the signal lines $2a$ and so as to surround the entire twisted signal wire 2. The plural power lines 4 are arranged so as to be located on one circle C1 concentric with the circle C2. In addition, in the present embodiment, each power line 4 is in contact with its adjacent power lines 4. In addition, in the present embodiment, the power lines 4 are arranged so that each power line 4 is also in contact with the twisted signal wire 2. Moreover, each of the plural power lines 4 has a smaller diameter than the twisted signal wire 2. Furthermore, it is preferable that all plural power lines 4 have the same diameter.

Each of the plural power lines 4 has a conductor 4(1) and an insulation layer 4(2) provided to surround the conductor 4(1), i.e., to cover the outer surface of the conductor 4(1). Each of the plural power lines 4 has a smaller diameter than the twisted signal wire 2.

As the conductor 4(1), it is possible to use, e.g., a copper wire or a copper alloy wire. The copper wire is more preferable than the copper alloy wire in view of high electrical conductivity, while the copper alloy wire is more preferable than the copper wire in view of high tensile strength.

Resistivity (conductivity) per power line 4 is adjusted so that an allowable current value of the composite cable 1 is a predetermined value. This adjustment can be performed by changing a radial cross-sectional area of the conductor of each power line 4 (hereinafter, also referred to as "conductor cross-sectional area of the power line 4") or a type (metal structure) of conductor.

For example, when the sum of the conductor cross-sectional areas of all power lines 4 (the total conductor cross-sectional area) is small and the allowable current value of the composite cable 1 is less than the predetermined value, the conductor cross-sectional area per power line 4 is (gradually) increased or the conductor is changed to a conductor having a higher conductivity. Alternatively, the allowable current value of the composite cable 1 may be adjusted by increasing (or decreasing) the number of the power lines 4. When the conductor cross-sectional area per power line 4 is increased or the number of the power lines 4 is increased, the diameter of the twisted signal wire 2 is increased by, e.g., adjusting the thickness of each signal line 2a or the thickness of the insert 3 so that all the power lines 4 can be arranged on one circle C1 concentric with the circle C2.

Meanwhile, when, for example, the total of the conductor cross-sectional areas of all power lines 4 is large and the allowable current value of the composite cable 1 is more than the predetermined value, the conductor cross-sectional area per power line 4 is (gradually) reduced or the conductor is changed to a conductor having a lower conductivity. In this case, however, no problem arises even when the total conductor cross-sectional area is not changed and is greater than the area providing the allowable current value required for the composite cable 1, i.e., even when the power line(s) 4 (conductor(s)) not transmitting power is included.

The insulation layer 4(2) is preferably, e.g., an enamel layer. In other words, it is preferable to use an enameled wire as the power line 4. The enamel layer can be formed of one or more of enamels selected from the group consisting of, e.g., polyimide (PI), polyamide-imide (PAI), polyesterimide (PEsI), polyetherimide (PEI), polyimide hydantoin-modified polyester, polyamide (PA), formal, polyurethane, polyester (PEst), polyvinyl formal, epoxy and polyhydantoin.

The thickness of the enamel layer (the cover film thickness) is set to be a thickness which allows the enameled wire to have resistance such as insulation resistance and heat resistance. Thus, the thickness of the enamel layer can be smaller than a thickness of an insulation layer of, e.g., an insulated wire core other than enameled wire.

The enamel layer is a layer having a high elongation and a high mechanical strength. While elongation at break of, e.g., a conductor not covered with an enamel layer (e.g., only a copper wire) is about 30 to 40%, elongation at break of the enameled wire is about 100 to 150%. As such, the enamel layer serves as a reinforcing layer (protective layer) for the conductor.

The plural power lines 4 can be divided into plural power line groups, such that one power line group consists of a predetermined number of power lines 4 adjacent to each other. Power line groups are configured so that the total conductor cross-sectional area of, e.g., one power line group is equivalent to the total conductor cross-sectional area of one power line in a conventional composite cable. In the present embodiment, for example, the power lines are divided into power line groups A to D each having six power lines 4, and power line groups E and F each having seven power lines 4, as shown in FIG. 1A. The number of the power line groups and the number of the power lines 4 consisting each power line group can be appropriately selected according to the intended use or the amount of power to be transmitted. A decrease in withstand voltage per power line 4 due to diameter reduction can be compensated when the power lines are grouped as described above.

The plural power lines 4 are preferably identifiable from each other. The power lines 4 are preferably identifiable by, e.g., tracer technique. Alternatively, the power lines 4 may be identifiable by, e.g., color coding using different colored insulation layers (enamel layers) or numbering the insulation layers. The power lines 4 may be configured such that, e.g., the color of the insulation layer is different for each of the power line groups A to F. Alternatively, for example, dummy wires color-coded to serve as markers may be provided between the power wire groups.

Figure 2:
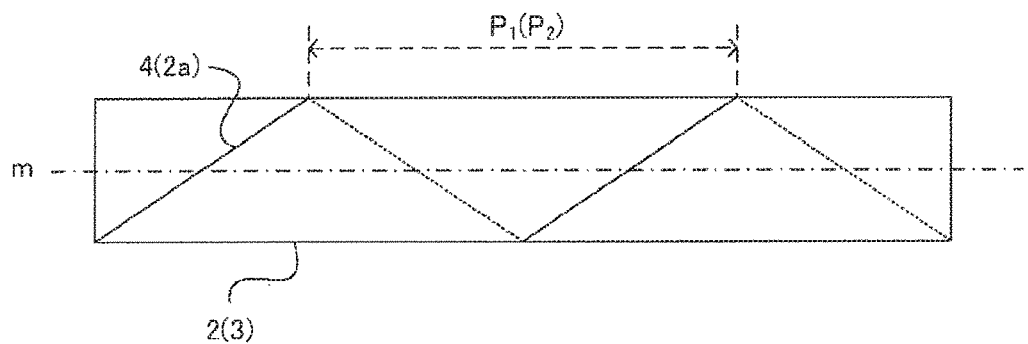
FIG. 2 is an exemplary schematic diagram illustrating a twist pitch of power lines (signal lines)

The plural power lines 4 are twisted together about the twisted signal wire 2, as described above. In this case, a lay ratio of the power lines 4 is preferably different from that of the twisted signal wire 2. That is, it is preferable that each power line 4 intersect with each signal line 2a. In detail, a ratio of a twist pitch $P_1$ of the power lines 4 to a pitch diameter $Pd_1$ of a layer formed of the power lines 4 (a $P_1/Pd_1$ ratio) is preferably different from a ratio of a twist pitch $P_2$ of the signal lines 2a to a pitch diameter $Pd_2$ of a layer formed of the signal lines 2a (a $P_2/Pd_2$ ratio), i.e., the $P_1/Pd_1$ ratio≠$P_2/Pd_2$ ratio. The pitch diameter of the layer formed of the power lines 4 here is a diameter of the above-described circle C1 (i.e., the circle C1 passing through the centers of the power lines 4), and the pitch diameter of the layer formed of the signal lines 2a is a diameter of the above-described circle C2. Then, the twist pitch $P_1$, $P_2$ is a distance required for each power line 4 or each signal line 2a to helically rotate 360° in the circumferential direction about the center axis m of the composite cable 1 (i.e., about the center axis of the insert 3 or the twisted signal wire 2), as shown in FIG. 2.

In addition, the power lines 4 are preferably twisted with a shorter pitch than the signal lines 2a. In other words, the $P_1/Pd_1$ ratio is preferably smaller than the $P_2/Pd_2$ ratio (i.e., the $P_1/Pd_1$ ratio<the $P_2/Pd_2$ ratio).

In addition, the configuration in which a twist direction of the power lines 4 is the same as a twist direction of the signal lines 2a is preferable in that change in the twisted state of the power lines 4 due to bending of the composite cable 1 is the same as change in the twisted state of the signal lines 2a. In other words, it is preferable because the twist of the signal lines 2a becomes loose when the twist of the power lines 4 becomes loose, and the twist of the signal lines 2a becomes tight when the twist of the power lines 4 becomes tight. Meanwhile, the configuration in which the twist direction of the power lines 4 is different from the twist direction of the signal lines 2a is preferable in that it is easy to intersect the power lines 4 and the signal lines 2a.

The twisted signal wire 2 and the plural power lines 4 may be covered with a binding tape 5, etc. The binding tape 5 is a resin tape for bundling the twisted signal wire 2 and the plural power lines 4. As the binding tape 5, it is possible to use a tape formed of, e.g., polytetrafluoroethylene (PTFE).

A shield layer (electromagnetic shielding layer) 6 is provide on the binding tape 5 so as to cover the outer circumferential surface of the binding tape 5. The shield layer 6 can be constructed from a served shield formed by spirally winding metal strands around the binding tape 5, a braided conductor formed by braiding multiple conductors, or a conductive tape having a conductive metal film on a resin tape. Use of the served shield as the shield layer 6 is more preferable since flex resistance of the composite cable 1 can be further improved.

An outer cover (sheath) 7 is provided on the shield layer 6 so as to cover the outer circumferential surface of the shield layer 6. The sheath 7 is the outermost layer of the composite cable 1.

The sheath 7 is formed of a resin material or a rubber material. When the composite cable 1 is used in, e.g., the endoscopic device described previously, the sheath 7 is preferably formed of a biocompatible resin material, etc. In other words, the sheath 7 is preferably formed of a resin material which is non-toxic and does not cause allergic symptoms such as inflammation upon contact with living organisms, for example, a highly biologically compatible resin material. In detail, the sheath 7 can be formed of a resin material (medical insulating resin, medical resin, medical grade resin) such as fluorine resin, e.g., PFA, or polyvinyl chloride (PVC), or a resin or rubber material consisting mainly of silicon (Si), such as silicon rubber. Of those, in view of biocompatibility and forming into a thin layer, a fluorine resin is preferably used as a resin material of the sheath 7 when the composite cable 1 is used in a medical device such as endoscopic device, i.e., used in clinical practice.

(2) Effects of the Present Embodiment

One or more effects described below are obtained in the present embodiment.

(a) It is possible to reduce the diameter of the composite cable 1 by arranging the plural power lines 4 so as to be located on the circumference of one circle C1 concentric with the circle C2 passing through the centers of the signal lines 2a and so as to surround the entire twisted signal wire 2. As a result, the composite cable 1 can have good flex resistance.

Figure 1B:
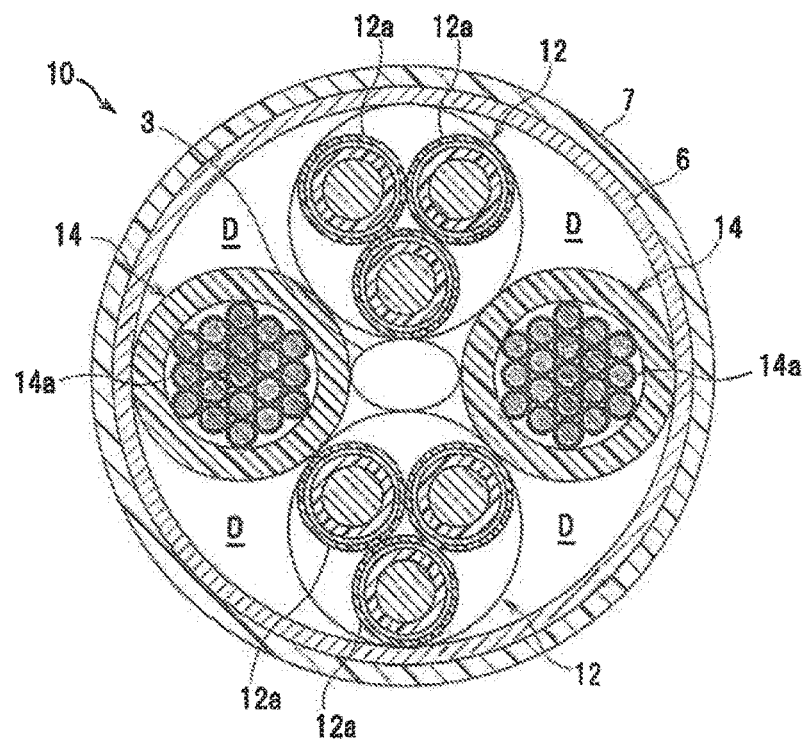
FIG. 1B is a schematic radial cross-sectional view showing a conventional composite cable.

(b) That is, by separately arranging the signal lines 2a and the power lines 4 respectively on the inner side and the outer side, it is possible to reduce a dead space D inside the composite cable 1 as compared to, e.g., a composite cable 10 shown in FIG. 1B which is configured that twisted signal wires 12 (signal lines 12a) and two power lines (insulated core wires) 14 each formed by twisting plural conductors 14a are arranged together and mixed in one layer (the twisted signal wires 12 and the power lines 14 are twisted together in a mixed state). Thus, the radial cross-sectional area of the composite cable 1 can be reduced. Here, the diameter and number of the signal lines 2a in the composite cable 1 shown in FIG. 1A are the same as the diameter and number of the signal lines 12a in the composite cable 10 shown in FIG. 1B. In addition, the total conductor cross-sectional area of the power lines 4 is the same as that of the power lines 14. In other words, the number of the power lines 4 is the same as the total number of the conductors 14a of the two power lines 14.

The reason why such effect can be obtained is as follows: a diameter of one power line 14 in the composite cable 10 shown in FIG. 1B is larger than a diameter of the power line 4 used in the composite cable 1 of the present embodiment. Since such thick power lines 14 and the twisted signal wires 12 are twisted together in a mixed state in the composite cable 10, i.e., since thick wires are twisted together, the dead space D formed in the composite cable 10 is large. In contrast, in the composite cable 1 of the present embodiment, the twisted signal wire 2 (the signal lines 2a) and the power lines 4 are separately arranged respectively on the inner side and the outer side. In this configuration, it is not necessary to twist the twisted signal wire with the thick power lines and the dead space D in the composite cable 1 thus can be smaller than the composite cable 10 shown in FIG. 1B, resulting in that the diameter of the composite cable 1 can be reduced.

It could be configured that power lines are arranged on the inner side of the composite cable and signal line are arranged to surround the all the power lines. However, in composite cables, the total radial cross-sectional area of the signal lines is generally smaller than the total radial cross-sectional area of the power lines. In this case, arranging the signal lines to surround all the power lines may reduce efficiency. In other words, the diameter of the composite cable may not be reduced. Therefore, it is preferable to arrange the twisted signal wire 2 on the inner side of the composite cable 1 and to separately arrange the power lines 4 around the twisted signal wire 2 as is in the present embodiment.

(c) Since the plural power lines 4 are arranged so as to be located on the circumference of one circle C1 concentric with the circle C2 passing through the centers of the signal lines 2a, all the power lines 4 provided in the composite cable 1 can have the same length. Flex resistance of the composite cable 1 thus can be further improved.

Figure 3:
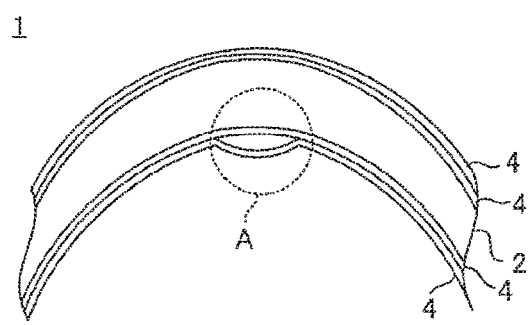
FIG. 3 is a schematic diagram illustrating a state in which a power line protrudes outward on the inner side of a bent portion when the composite cable is bent.
Figure 4:
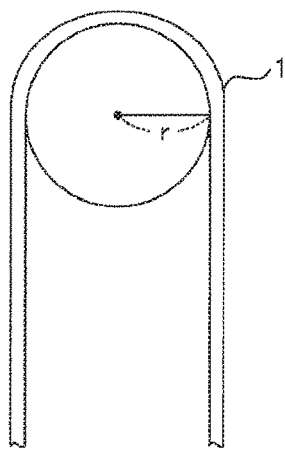
FIG. 4 is an exemplary schematic diagram illustrating a bend radius r of the composite cable.

The reason is as follows: the power lines 4 are twisted about the twisted signal wire 2, as described above. In this case, if the power lines 4 are arranged on two or more circles which are concentric with the circle C2, a winding diameter of the power lines 4 arranged on the circumference of the outer circle is larger than that of the power lines 4 arranged on the circumference of the inner circle. This results in that when the twist pitch $P_1$ of the power lines 4 respectively arranged on the circumference of the outer circle and the circumference of the inner circle is the same, the longitudinal length (a length in a direction orthogonal to the radial direction) of the power lines 4 arranged on the circumference of the outer circle is larger than that of the power lines 4 arranged on the circumference of the inner circle. When the composite cable 1 having such plural power lines 4 with different lengths is bent, a longer power line 4 comes out on the inner side of the bent portion and protrudes toward the outside (toward the outer periphery) of the composite cable 1 (see the portion A circled by a dotted line in FIG. 3). Since structural components such as the binding tape 5, the shield layer 6 and the sheath 7, etc., are provided around the power lines 4, the protruding power line 4 is pressed down by such structural components when the composite cable 1 is bent. Thus, when the composite cable 1 is repeatedly bent, the power line 4 is kinked and snapped (broken). The smaller the bend radius r (see FIG. 4) of the bent composite cable 1, the more pronounced this phenomenon becomes. Kinking of the power line 4 here means that the power line 4 is twisted, distorted, curled, bulges, bent or squashed, etc.

In contrast, in the present embodiment, the plural power lines 4 are arranged so as to be located on the circumference of one circle C1 concentric with the circle C2. This allows all the power lines 4 of the composite cable 1 to have the same length (the lengths which can be regarded as the same) in the longitudinal direction. Thus, when the composite cable 1 is bent, any specific one of the power lines 4 is less likely to protrude and less likely to be pressed down by the structural components. Therefore, the power lines 4 are less likely to be kinked even when the composite cable 1 is repeatedly bent, resulting in that breakage (fracture) of the power lines 4 can be prevented. In other words, it is possible to improve flex resistance of the composite cable 1.

To further reduce the dead space and a diameter of the composite cable, the embodiment could be configured that the power lines are arranged to fill the dead space formed due to the twisted signal wire. However, in the present embodiment, the diameter of the power line is smaller than the diameter of the twisted signal wire, as described above. Therefore, if the power lines are arranged to fill the dead space, the power lines may be compressed by the twisted signal wire when the composite cable is bent. In addition, when the composite cable is bent in this case, a power line(s) may moves toward the outside (toward the outer periphery) of the composite cable or may be trapped and compressed in a gap between a structural component such as the binding tape 5 and the twisted signal wire. When the composite cable is repeatedly bent in such state, the power lines are likely to be kinked and broken.

(d) Since the plural power lines 4 are arranged so as to surround the entire twisted signal wire 2, each power line 4 can have a smaller diameter. In the composite cable 1 of the present embodiment, a diameter of one power line 4 can be smaller than a power line of, e.g., the composite cable 10 in which the twisted signal wires 12 and the power lines 14 are mixed and twisted together as shown in FIG. 1B. When providing the same total conductor cross-sectional area, the conductor cross-sectional area per power line 4 can be reduced by arranging the power lines 4 as described above and can be smaller than the power line 14 of the composite cable 10 shown in FIG. 1B.

By reducing the diameter of each power line 4 as such, it is possible to reliably improve flex resistance of the composite cable 1. The reason is as follows: when power lines 4 with various diameters are bent with a certain bend radius r, strain generated in the bent portion is smaller in the power line 4 with a smaller diameter. This means that the power lines 4 with a smaller diameter are less likely to be broken even when the composite cable 1 is repeatedly bent. Therefore, it is possible to further improve flex resistance of the composite cable 1 by reducing the diameter of the power lines 4.

(e) In addition, since the plural power lines 4 are arranged so as to surround the entire twisted signal wire 2, it is possible to disperse stress applied to each power line 4 at a bent portion when the composite cable 1 is bent. Therefore, the power lines 4 are less likely to be broken even when the composite cable 1 is repeatedly bent, and it is thereby possible to further improve flex resistance of the composite cable 1.

(f) The adjacent power lines 4 are in contact with each other. Therefore, when the composite cable 1 is bent, the contact between the adjacent power lines 4 prevents the power lines 4 from moving inside the composite cable 1. This prevents a specific power line 4 from, e.g., being kinked or caught by another structural component (e.g., caught between the twisted signal wire 2 and the binding tape 5 or the shield layer 6, etc.). As a result, it is possible to prevent a phenomenon in which the power line 4 caught by a structural component is compressed by the structural component when the composite cable 1 is bent. Therefore, the power lines 4 are more unlikely to be broken even when the composite cable 1 is repeatedly bent, and it is thereby possible to improve flex resistance of the composite cable 1 more reliably.

(g) An enameled wire is used as the power line 4. Therefore, the insulation layer is thinner than when using another insulated wire core and the composite cable 1 thus can have a smaller diameter. In addition, since the conductor and the enamel layer in the enameled wire are bonded, the enameled wire has a higher elongation at break than an insulated wire core having a conductor not bonded to an insulation layer and is thus more excellent in flex resistance.

(h) Since each power line 4 has the same diameter, it is possible to prevent a phenomenon in which a specific power line 4 is compressed by other power lines 4 when the composite cable 1 is bent. Thus, it is possible to prevent a specific power line 4 from being kinked and broken even when the composite cable 1 is repeatedly bent. As a result, it is possible to improve flex resistance of the composite cable 1 further reliably.

(i) The $P_1/Pd_1$ ratio is different from the $P_2/Pd_2$ ratio (the $P_1/Pd_1$ ratio≠the $P_2/Pd_2$ ratio) so that each power line 4 intersects with each signal line 2a. Therefore, even if one of the signal lines 2a is pulled and a groove (gap) is formed between adjacent signal lines 2a when the composite cable 1 is bent, the power line 4 can be prevented from falling into such groove. When the composite cable 1 is bent in a state that the power line 4 is caught in such groove, a specific power line 4 (e.g., the power line 4 caught between the signal lines 2a) may be compressed by another power line 4 or the twisted signal wire 2. In the present embodiment, such state can be prevented from occurring when the composite cable 1 is bent. As a result, it is possible to reliably prevent a specific power line 4 from being compressed, kinked and broken even when the composite cable 1 is repeatedly bent. In other words, it is possible to improve flex resistance of the composite cable 1 further reliably.

On the other hand, if the $P_1/Pd_1$ ratio and the $P_2/Pd_2$ ratio are equal to each other (the $P_1/Pd_1$ ratio=the $P_2/Pd_2$ ratio), the power lines 4 are arranged respectively parallel to the signal lines 2a and the power line 4 may fall into a groove between adjacent signal lines 2a even when the composite cable 1 is not bent. As a result, a specific power line 4 may be compressed by another power line 4 or the twisted signal wire 2 and may be broken as described above.

(j) The configuration of the $P_1/Pd_1$ ratio<the $P_2/Pd_2$ ratio can improve flex resistance of the composite cable 1 further reliably.

The reason is as follows: the composite cable 1 when bent may be turned around, and this may result in that the power lines 4 and the signal lines 2a (the twisted signal wire 2) are also turned around (turn is applied). This may cause the twist pitches $P_1$ and $P_2$ of the power lines 4 and the signal lines 2a to change and the twist of the power lines 4 or the signal lines 2a to become loose or tight. In other words, the twisted state (the turned state) of the power lines 4 and the signal lines 2a (the twisted signal wire 2) may change due to bending of the composite cable 1. In this case, with the $P_1/Pd_1$ ratio>the $P_2/Pd_2$ ratio, the power line 4 may fall and be caught in a groove formed between adjacent signal lines 2a when the composite cable 1 is bent and the power lines 4 and the twisted signal wire 2 are turned around in, e.g., a direction in which the twist thereof becomes loose (a direction in which the twist pitches $P_1$ and $P_2$ of the power lines 4 and the signal lines 2a become short). In contrast, with the $P_1/Pd_1$ ratio<the $P_2/Pd_2$ ratio, it is possible to prevent the power line 4 from falling and being caught in a groove formed between adjacent signal lines 2a even when the twisted state of the power lines 4 and the signal lines 2a changes due to bending of the composite cable 1. As a result, it is possible to obtain the effect (j) more reliably.

(k) In addition, since the $P_1/Pd_1$ ratio<the $P_2/Pd_2$ ratio, a longitudinal length per power line 4 (a length of the power line 4) is larger than a longitudinal length per signal line 2a (a length of the signal line 2a). That is, in the composite cable 1, the power lines 4 located on the outer side are longer than the signal lines 2a located on the inner side. Since the power lines 4 have an extra length, the composite cable 1 becomes more flexible, breakage of the power lines 4 can be prevented more reliably, and flex resistance of the composite cable 1 can be improved further reliably.

(l) In addition, since the $P_1/Pd_1$ ratio<the $P_2/Pd_2$ ratio, it is possible to adequately prevent the signal lines 2a located on the inner side from being excessively pulled even when, e.g., bending of the composite cable 1 causes the power lines 4 and the signal lines 2a to be turned around in a direction in which the twist pitches $P_1$ and $P_2$ become short. Therefore, a tensile force applied to the power lines 4 due to pulling of the signal lines 2a can be reduced, resulting in that it is possible to prevent breakage of the power lines 4 and thus possible to reliably improve flex resistance of the composite cable 1.

On the other hand, when the power lines 4 are twisted with a longer pitch than the signal lines 2a (the $P_1/Pd_1$ ratio>the $P_2/Pd_2$ ratio), the power lines 4 are shorter than the signal lines 2a. In this case, the composite cable 1 becomes less flexible and the power lines 4 are more likely to be broken than when the $P_1/Pd_1$ ratio<the $P_2/Pd_2$ ratio. In addition, the signal lines 2a located on the inner side are excessively pulled when, e.g., bending of the composite cable 1 causes the power lines 4 and the signal lines 2a to be turned around in a direction in which the twist pitches $P_1$ and $P_2$ become short. Thus, the above-mentioned tensile force applied to the power lines 4 increases and the power lines 4 are likely to be broken.

(m) The composite cable 1 in the present embodiment is effectively used particularly for connecting portions between which sharp bend (with a small bend radius r) is repeatedly applied. The composite cable 1 in the present embodiment can be suitably used in, e.g., an endoscopic device. In detail, the composite cable 1 in the present embodiment can be suitably used to connect a camera head to a control unit in an endoscopic device.

Other Embodiments of the Invention

Although the embodiment of the invention has been specifically described, the invention is not to be limited to the embodiment and can be appropriately changed without departing from the gist thereof.

Although the example in which each power line 4 is in contact with the adjacent power lines 4 has been described in the embodiment, it is not limited thereto. That is, the adjacent power lines 4 may not be in contact with each other as long as the plural power lines 4 are arranged so as to be located on the circumference of the circle C1 concentric with the circle C2. In the composite cable 1, however, the signal lines 2a and the power lines 4 need to be arranged in a well-balanced manner to some extent so that both mechanical performance and electrical performance can be obtained. To obtain both in this case, it is preferable that the adjacent power lines 4 be spaced at equal intervals, i.e., plural power lines 4 be evenly arranged in the radial direction of the composite cable 1.

EXAMPLE

The test results confirming the effects obtained in the embodiment will be described below.

A twisted wire in Example was formed by twisting a (six-core) twisted signal wire composed of six twisted coaxial lines (signal lines) and thirty-eight power lines (38 cores) arranged so as to be located on a circumference of a circle concentric with the twisted signal wire and so as to surround the entire twisted signal wire as shown in FIG. 1A. The coaxial line used in this Example was a wire which has a (inner) conductor, an insulation layer (non-conductor) provided to surround the inner conductor, an outer conductor formed on the insulation layer by spirally winding metal strands, and an insulation layer (jacket) provided to surround the outer conductor. The power line used was an enameled wire having a conductor and an enamel layer provided to surround the conductor.

Following is the detailed specifications of the coaxial line and the power line used in Example.
Coaxial Line
  (Inner) Conductor size: 44 AGW
  Outer diameter φ of Coaxial line: 0.258 mm
  Inner conductor configuration: a twisted wire composed of seven conductors, outer diameter of each conductor is 0.02 mm
  Thickness of Insulation layer (non-conductor): 0.054 mm
  Outer conductor: served, strand diameter 0.02 mm
  Thickness of Jacket: 0.025 mm
Power Line (Enameled Wire)
  Outer diameter φ of Conductor: 0.05 mm
  Thickness of Insulation layer: 0.005 mm
  Outer diameter φ of Enameled wire: 0.06 mm
  The outer diameter (overall outer diameter) of the twisted wire in Example was 0.90 mm.

A twisted wire in Comparative Example was formed by twisting six coaxial wires and two insulated wire cores (two cores) as shown in FIG. 1B.

In Comparative Example, the coaxial line was the same as that in Example and the power line was an insulated wire core having a conductor and an insulation layer provided to surround the conductor. Following is the detailed specification of the insulated wire core used in Comparative Example.
Power Line (Insulated Wire Core)
  Conductor size: 32 AGW
  Outer diameter φ: 0.37 mm
  Conductor configuration: a twisted wire composed of nineteen conductors, outer diameter of each conductor is 0.05 mm
  Thickness of Non-conductor (Insulation layer): 0.06 mm
  The outer diameter (overall outer diameter) of the twisted wire in Comparative Example was 1.12 mm.

The outer diameter of the twisted wire in Example was reduced by about 20% as compared to the twisted wire in Comparative Example even though the number of the coaxial lines and the total conductor cross-sectional area of the power lines were the same. In other words, the radial cross-sectional area was successfully reduced. Therefore, a composite cable formed by providing structural components such as binding tape, shield layer and sheath around the twisted wire in Example can have a smaller diameter than a composite cable formed in the same manner using the twisted wire in Comparative Example.

Preferred Embodiments of the Invention

Preferred embodiments of the invention will be described below.

[1] An aspect of the invention provides a composite cable, comprising: a twisted wire formed by twisting a plurality of signal lines; and a plurality of power lines that are arranged on a circumference of a circle concentric with the twisted wire so as to surround an outer circumference of the twisted wire and are twisted around the twisted wire.

[2] In the composite cable defined by [1], preferably, the power line comprises an enameled wire, and the signal line comprises a coaxial line.

[3] In the composite cable defined by [1] or [2], preferably, a ratio of a twist pitch ($P_1$) of the power lines to a pitch diameter ($Pd_1$) of a layer formed of the power lines (a $P_1/Pd_1$ ratio) is different from a ratio of a twist pitch ($P_2$) of the signal lines to a pitch diameter ($Pd_2$) of a layer formed of the signal lines (a $P_2/Pd_2$ ratio).

[4] In the composite cable defined by [3], preferably, a ratio of a twist pitch ($P_1$) of the power lines to a pitch diameter ($Pd_1$) of a layer formed of the power lines (a $P_1/Pd_1$ ratio) is smaller than a ratio of a twist pitch ($P_2$) of the signal lines to a pitch diameter ($Pd_2$) of a layer formed of the signal lines (a $P_2/Pd_2$ ratio).

[5] In the composite cable defined by any one of [1] to [4], preferably, a twist direction of the signal lines is the same as a twist direction of the power lines.

[6] In the composite cable defined by any one of [1] to [4], preferably, a twist direction of the signal lines is different from a twist direction of the power lines.

[7] In the composite cable defined by any one of [1] to [6], preferably, the plurality of power lines have the same diameter.

[8] In the composite cable defined by any one of [1] to [7], preferably, the adjacent power lines are in contact with each other.

[9] In the composite cable defined by any one of [1] to [8], preferably, the plurality of power lines are divided into a plurality of power line groups such that one power line group consists of a predetermined number of adjacent power lines.

[10] The cable defined by any one of [1] to [9] is preferably used in an endoscopic device.

What is claimed is:

1. A composite cable, comprising:
   a twisted wire formed by twisting a plurality of signal lines; and
   a plurality of power lines that are arranged on a circumference of a circle concentric with the twisted wire so as to surround an outer circumference of the twisted wire and are twisted around the twisted wire,
   wherein each signal line of the signal lines comprises a conductor, an insulation layer provided around the conductor, a shield provided around the insulation layer, and a jacket provided around the shield,
   wherein each power line of the power lines comprises a conductor and an enamel layer comprising one or more of enamels selected from the group consisting of polyimide (PI), polyamide-imide (PAI), polyesterimide (PEsI), polyetherimide (PEI), polyimide hydantoin-modified polyester, polyamide (PA), formal, polyurethane, polyester (PEst), polyvinyl formal, epoxy and polyhydantoin,
   wherein said each power line has a smaller diameter than said each signal line, and
   wherein a ratio of a twist pitch of the power lines to a pitch diameter of a layer formed of the power lines is smaller than a ratio of a twist Ditch of the signal lines to a pitch diameter of a layer formed of the signal lines.

2. The composite cable according to claim 1, wherein said each power line comprises an enameled wire, and said each signal line comprises a coaxial line.

3. The composite cable according to claim 2, wherein a twist direction of the signal lines is a same as a twist direction of the power lines.

4. The composite cable according to claim 2, wherein a twist direction of the signal lines is different from a twist direction of the power lines.

5. The composite cable according to claim 1, wherein a twist direction of the signal lines is a same as a twist direction of the power lines.

6. The composite cable according to claim 1, wherein a twist direction of the signal lines is different from a twist direction of the power lines.

7. The composite cable according to claim 1, wherein said each power line is in a direct contact with adjacent power lines of said power lines.

8. The composite cable according to claim 1, wherein the power lines are in a direct contact with the signal lines.

9. The composite cable according to claim 1, wherein the jacket of said each signal line is in a direct contact with the power lines.

10. The composite cable according to claim 1, wherein the jacket of said each signal line abuts the enamel layer of the power lines.

* * * * *